United States Patent
Kuo

(10) Patent No.: US 8,298,214 B2
(45) Date of Patent: Oct. 30, 2012

(54) VISION CORRECTION SYSTEM AND OPERATING METHOD THEREOF

(75) Inventor: I-Ku Kuo, Thaipao (TW)

(73) Assignee: Kera Harvest Inc., Thaipao, Chiai County (TW)

(*) Notice: Subject to any disclaimer, the term of this patent is extended or adjusted under 35 U.S.C. 154(b) by 458 days.

(21) Appl. No.: 12/644,908

(22) Filed: Dec. 22, 2009

(65) Prior Publication Data

US 2011/0152846 A1    Jun. 23, 2011

(51) Int. Cl.
*A61B 18/18* (2006.01)
(52) U.S. Cl. .................. 606/5; 606/4; 606/12
(58) Field of Classification Search ............... 606/4–6, 606/10–12; 607/88–95; 351/205–212
See application file for complete search history.

(56) References Cited

U.S. PATENT DOCUMENTS

| | | | | | |
|---|---|---|---|---|---|
| 5,795,351 | A | * | 8/1998 | Clapham | 606/4 |
| 7,584,756 | B2 | * | 9/2009 | Zadoyan et al. | 128/898 |
| 7,837,091 | B2 | * | 11/2010 | Cook et al. | 235/375 |

* cited by examiner

*Primary Examiner* — Mohammed Hasan
(74) *Attorney, Agent, or Firm* — Morris Manning & Martin LLP; Tim Tingkang Xia, Esq.

(57) ABSTRACT

A vision correction system and an operating method thereof are provided. The vision correction system includes an evaluation device and a correction device. The evaluation device scans an eyeball of a person and records a spherical curvature of a cornea of the eyeball as an evaluation data. The correction device includes an operation unit for receiving the evaluation data recorded by the evaluation device, and operating on and converting the evaluation data into a correction data. The correction device further includes a laser unit controlled by the operation unit for respectively forming a correction area and a prevention area on the cornea of the eyeball of the person according to the correction data. The prevention area is formed as multiple convex arcs outwards from the correction area of the cornea of the eyeball, and each of convex arcs has a different radius.

14 Claims, 5 Drawing Sheets

VISION CORRECTION SYSTEM AND OPERATING METHOD THEREOF

BACKGROUND OF THE INVENTION

1. Field of Invention

The present invention relates to a vision correction system and an operating method thereof, and more particularly to the technology of using a laser unit for performing a treatment on an eyeball of a person to form a correction area and a prevention area on the eyeball, so as to correct vision, but also solve a presbyopia problem occurring as eyeball functions degenerate.

2. Related Art

Referring to FIG. 1, the process in which a normal human eye receives light and generates an image is usually as follows. The light is refracted by the cornea 2 and passes through a pupil 3 of an eyeball 1. By the function of an iris 5, the pupil 3 dilates or constricts to regulate the amount of incoming light. Then, a crystalline lens 4 of the eyeball 1 refracts the light to focus images on a retina 6, and the images are transmitted to the brain via an optic nerve 7. The spherical curvature of the cornea 2 is very important, because ⅔ of eyes' focusing is achieved by the cornea 2. If the cornea 2 functions normally, it can refract light correctly to allow images to focus clearly on the retina 6. However, if the cornea 2 or the crystalline lens 4 fails to regulate light properly, a blurry vision will occur as images no longer focus correctly on the retina 6.

Referring to FIG. 2, the cornea 2 shown in FIG. 2 has a larger spherical curvature than that of the normal cornea 2, so that the cornea 2 refracts the entering light to focus in front of the retina 6. As a result, distant object images cannot be seen clearly, which is usually called myopia. Referring to FIG. 3, the cornea 2 shown in FIG. 3 has a smaller spherical curvature than that of the normal cornea 2, so that the cornea 2 refracts the entering light to focus behind the retina 6. As a result, nearby object images cannot be seen clearly, which is usually called hyperopia. In addition, referring to FIG. 4, a non-uniform spherical curvature of the cornea 2 shown in FIG. 4 causes astigmatism result in the inability to focus clearly at any distance.

In addition to the above problems caused by the spherical curvature of the cornea, when the elasticity of the crystalline lens of the eye gradually decreases or the contraction ability of the ciliary muscles deteriorates with age, the focusing ability of the eyeball becomes poorer and causes nearby objects to look blurry, which is called presbyopia. Moreover, when people with myopia getting older, they are still susceptible to presbyopia because of degeneration of their eye functions.

All the abovementioned diseases resulting from abnormal focusing in the eyes are generally referred to as refractive errors. In order to improve the focusing function, such refractive errors can now be treated through an excimer laser surgery in addition to the conventional correction methods such as wearing glasses or contact lenses. Since its success in the former Soviet Union more than 40 years ago, the excimer laser refractive surgery for refractive errors has been developed from the original radial keratotomy (RK) and photorefractive keratectomy (PRK) correction methods to the laser assisted in-situ keratomileusis (LASIK) technology which combines advantages of the RK and PRK surgeries. The new surgery method is safer and more effective, and provides patients with a fast and convenient post-surgery operation. However, with more and more patients with refractive errors receiving the laser surgery, the safety concerns vanish gradually, and the new generation laser surgery has currently become the main option for vision correction treatment as the operation time is reduced, the safety is higher, and the post-surgery treatment is simpler. The number of patients with the refractive errors receiving the LASIK surgery in the U.S. alone was as high as 2.5 million in 2007.

Referring to FIG. 5, laser beam is used to vaporize and remove a thin layer of tissues in the center of the cornea 2 so as to flatten the radian of the center of the cornea, thereby achieving the purpose of correcting myopia by correcting dioptric imaging of the light. The surgery method is capable to correct myopia of dioptric values ranging from −1.0 to −20.0 without reducing the robustness of the eyeballs or producing sequelae such as nyctalopia and hemeralopia, thereby significantly increasing the safety and precision of myopia correction. Besides, the surgery method is also applicable to the correction of hyperopia and astigmatism.

People receiving such surgery may well expect a life time of improved eyesight without wearing glasses in the following five to ten years; however, the modulation of their eyeballs still degenerates due to age, and presbyopia is increased and the same as hyperopia and astigmatism.

In addition to correction surgeries performed on patients with myopia, corrective treatment applicable to patients with hyperopia and astigmatism has been developed currently. In spite of outstanding achievements in treatment of the refraction error of myopia, the laser refractive treatment for refractive errors faces a lot of challenges in refractive error correction of presbyopia.

SUMMARY OF THE INVENTION

In view of the above problem, the present invention is directed to a vision correction system and an operating method thereof, which are capable of correcting vision of a person, and solving a vision problem of presbyopia occurring as eyeball functions degenerate.

In order to achieve the above objectives, the present invention provides a vision correction system, which includes an evaluation device and a correction device. The evaluation device scans an eyeball of a person, and records a spherical curvature of a cornea of the eyeball as an evaluation data. The correction device includes an operation unit and a laser unit. The operation unit receives the evaluation data recorded by the evaluation device, and operates on and converts the evaluation data into a correction data. The laser unit is controlled by the operation unit, and respectively forms a correction area and a prevention area on the eyeball of the person according to the correction data. The prevention area is formed as multiple convex arcs outwards from the periphery of the correction area, each having a different radius.

To sum up, in the present invention, a laser unit is used to form multiple convex arcs on a cornea of an eyeball of a person so that the healthy person or the person with refractive errors can overcome the trouble that presbyopia grows with age in advance; the prevention technique using multiple convex arcs enables the corrected cornea to solve the problem of presbyopia deterioration as a result of aging of the crystalline lens, and enables the person to keep the vision at the level after the correction surgery for a long time.

BRIEF DESCRIPTION OF THE DRAWINGS

The present invention will become more fully understood from the detailed description given herein below for illustration only, and thus are not limitative of the present invention, and wherein.

DETAILED DESCRIPTION OF THE INVENTION

Figure 1:
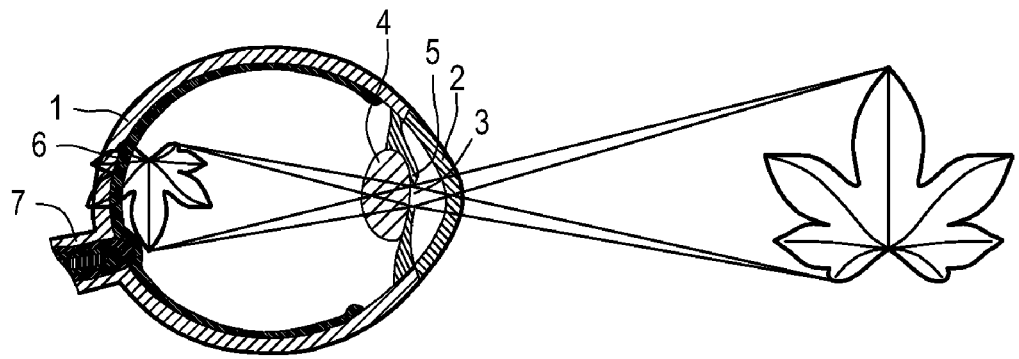
FIG. 1 is an illustration of projection of an object on a normal eyeball.
Figure 2:
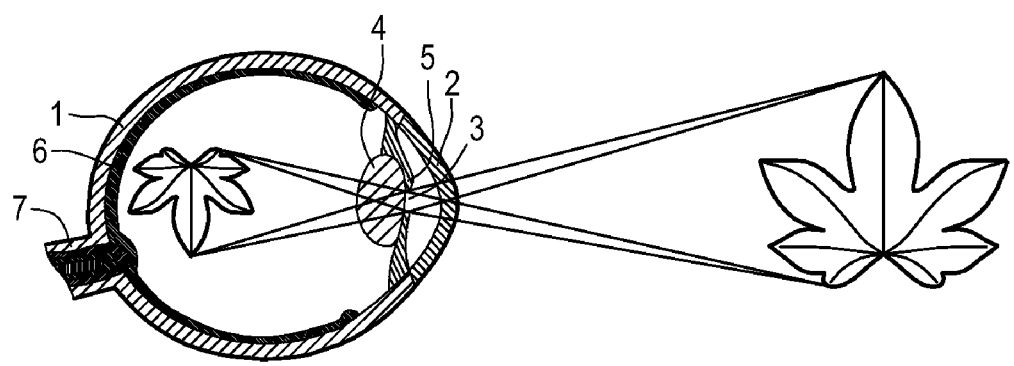
FIG. 2 is an illustration of projection of an object on an eyeball with myopia.
Figure 3:
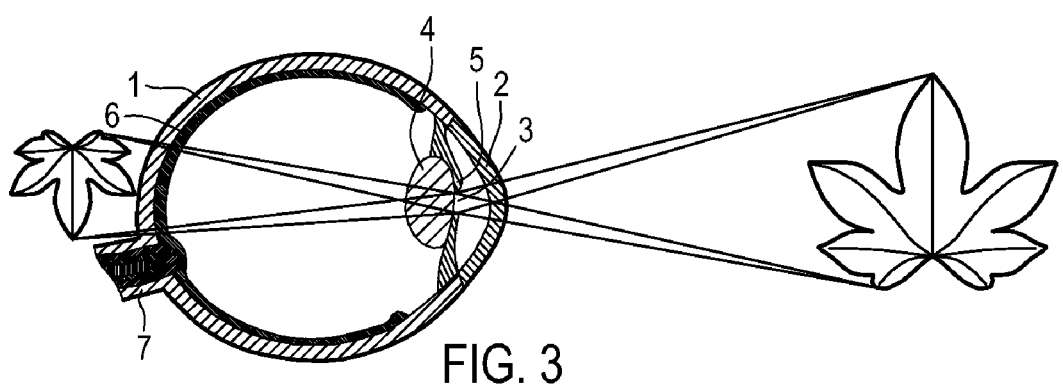
FIG. 3 is an illustration of projection of an object on an eyeball with hyperopia.
Figure 4:
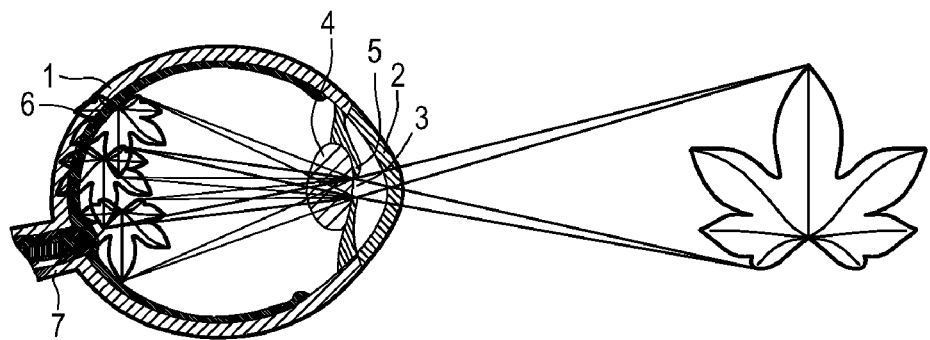
FIG. 4 is an illustration of projection of the object on an eyeball with astigmatism.
Figure 5:
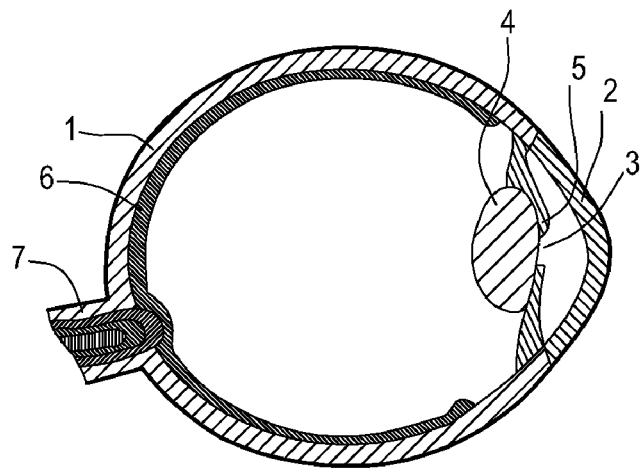
FIG. 5 is an illustration of an eyeball after a conventional myopia surgery.

A vision correction system and an operating method thereof according to a preferred embodiment of the present invention are illustrated below with reference to the accompanying drawings, in which like reference numerals are used to indicate like elements.

Figure 6:
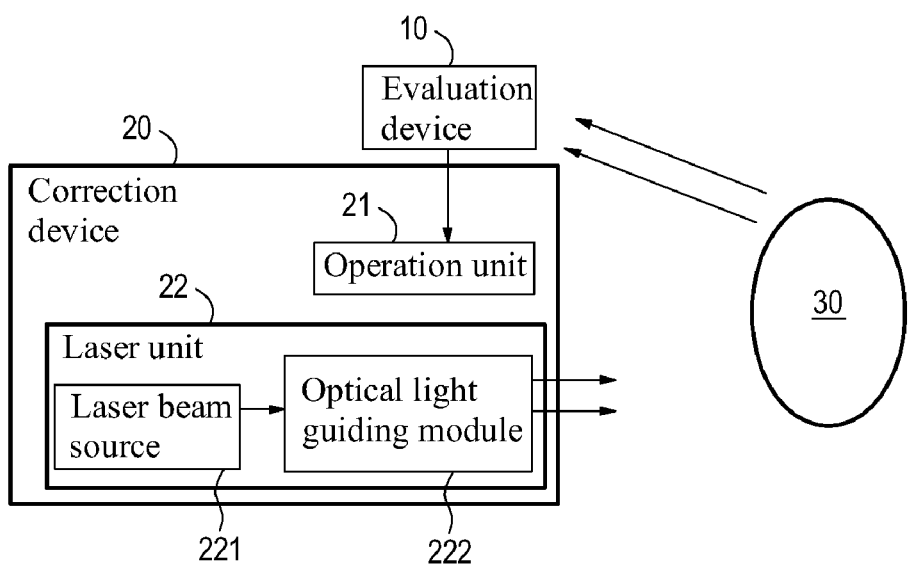
FIG. 6 is a structural view of a vision correction system in the present invention.

FIG. 6 is a structural view of the vision correction system in the present invention. Referring to FIG. 6, the vision correction system includes an evaluation device 10 and a correction device 20. The evaluation device 10 scans an eyeball 30 of a person, and records a spherical curvature of a cornea of the eyeball 30 as an evaluation data. The correction device 20 has an operation unit 21 and a laser unit 22. The operation unit 21 receives the evaluation data recorded by the evaluation device, and operates on and converts the evaluation data into a correction data. The laser unit 22 is controlled by the operation unit 21, and respectively forms a correction area and a prevention area on the eyeball of the person according to the correction data.

The laser unit 22 includes a laser beam source 221 for generating an appropriate amount of laser energy. The laser unit 22 further includes an optical light guiding module 222 for dispersing laser energy distribution and focusing the laser energy at one point. Further, if the correction device 20 is implemented as an argon fluoride excimer laser machine, and has an excimer laser therein in this embodiment, the laser beam source 221 can generate a laser beam that is split by the optical light guiding module 222 into a plurality of light beams to project on the eyeball. The light beams may be sequentially or randomly projected, and are projected on both the correction area and the prevention area simultaneously.

Figure 7:
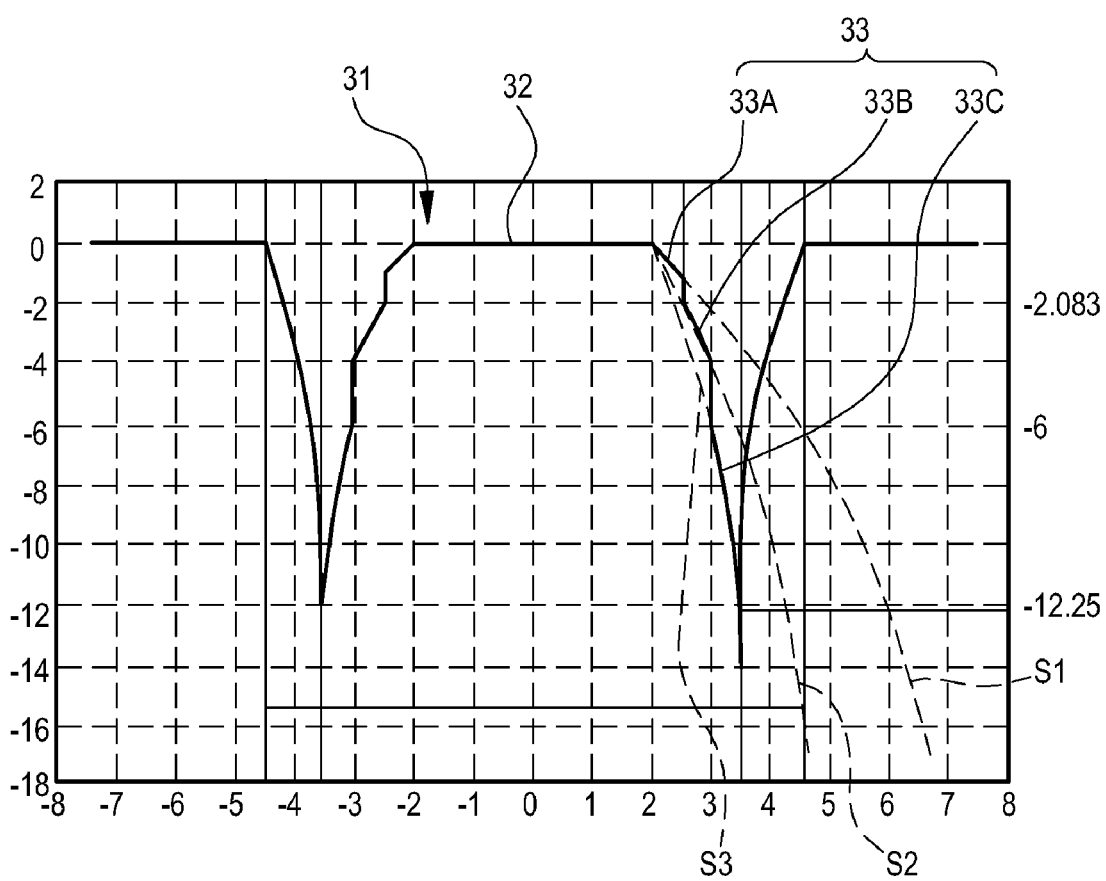
FIG. 7 is an illustration of forming a prevention area on an eyeball in the vision correction system in the present invention.

The formation of the prevention area on the eyeball of the person by using the above system is illustrated below with reference to FIG. 7. As shown in FIG. 7, the correction area 32 is defined within a radius of 2 mm from the center of the cornea 31 of the eyeball 30. Different surface curvatures may be applied according to different types of refractive errors of the person. The correction area 32 is implemented as a flat surface as shown in FIG. 7, which indicates a cornea without refractive errors or a cornea on which an astigmatism laser treatment has been applied. Furthermore, the prevention area 33 is defined as a ring area around the center of the cornea 31 and having an inner radius of 2 mm and an outer radius of 305 mm. In this embodiment, the prevention area 33 is formed by convex arcs 33A, 33B, and 33C cutting outward from the correction area 32 at every 0.2 to 0.5 mm with different curvatures S1, S2, and S3, and each of the convex arcs 33A, 33B, and 33C has a different radius. Finally, a transition area is defined at a radius of 3.5 to 4.5 mm from the center of the cornea 31.

A first curvature data is pre-calculated by the evaluation device 10 from the periphery of the correction area 32, and then the first convex arc 33A having a curvature S1 is formed by cutting the periphery of the correction area 32 according to the first curvature data by the laser unit 22. Further, a second curvature data is pre-calculated by the evaluation device 10 from the periphery of the first convex arc 33A, and then a second convex arc 33B having a curvature S2 is formed by cutting the periphery of the first convex arc 33A according to the second curvature data by the laser unit 22. Finally, a third curvature data is pre-calculated by the evaluation device 10 from the periphery of the second convex arc 33B, and then a third convex arc 33C having a curvature S3 is formed by cutting the periphery of the second convex arc 33B according to the third curvature data by the laser unit 22.

It should be noted that the convex arcs 33A, 33B, and 33C may not only be formed separately according to each curvature data, but they may also be formed in a single operation by the laser unit 22 after the evaluation device 10 evaluates and divides the eyeball 30 into the correction area and the prevention area in advance and calculates to obtain the curvature data.

Figures 8, 9:
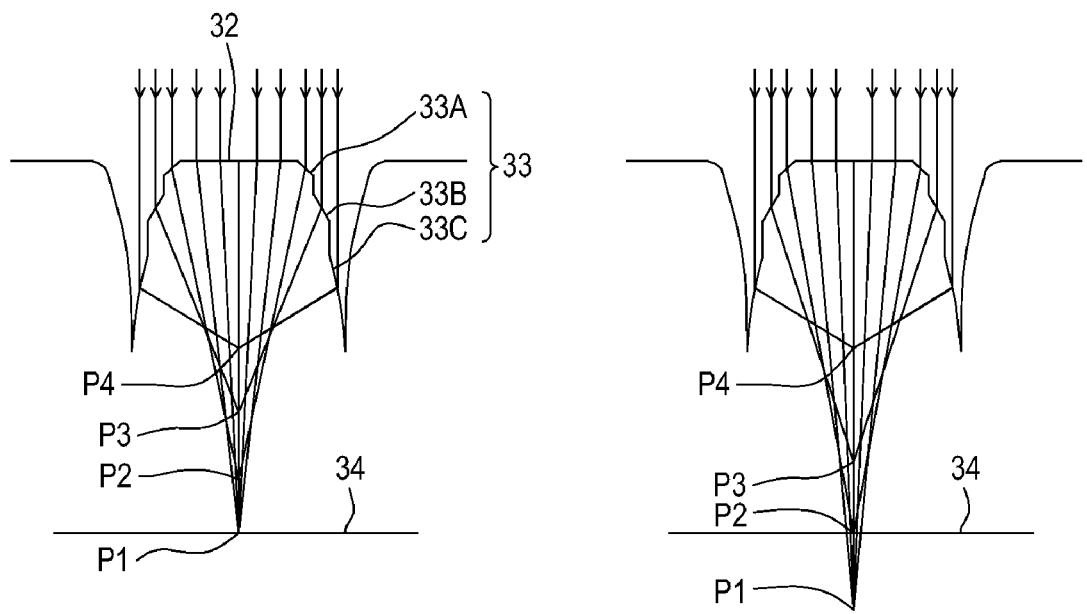
FIG. 8 is an illustration of imaging of light incident on a cornea in the present invention.
FIG. 9 is an illustration of imaging of light incident on an aging cornea in the present invention.

FIG. 8 is an illustration of imaging of light incident on the cornea. As shown in FIG. 8, the light incident through the correction area 32 of the cornea 31 is focused on a first imaging focal point P1 on a retina 34 to form a clear image; the light passing through the first convex arc 33A is focused on a second imaging focal point P2; the light passing through the second convex arc 33B is focused on a third imaging focal point P3; and the light passing through the third convex arc 33C is focused on a fourth imaging focal point P4. The second to the fourth imaging focal points P2 to P4 are all located in front of the retina 34, which are new imaging focal points for preventing aging of the cornea 31.

FIG. 9 is an illustration of imaging of light entering an aging cornea. As shown in FIG. 9, after the cornea 31 has aged, the imaging focal point of the retina 34 is the second imaging focal point P2 at which a clear image may be generated. That is, if the person has slight presbyopia in the future so that nearby objects will look blurred, the first convex arc 33A images the image on the retina 34 exactly, so as to eliminate the problem of presbyopia.

Figure 10:
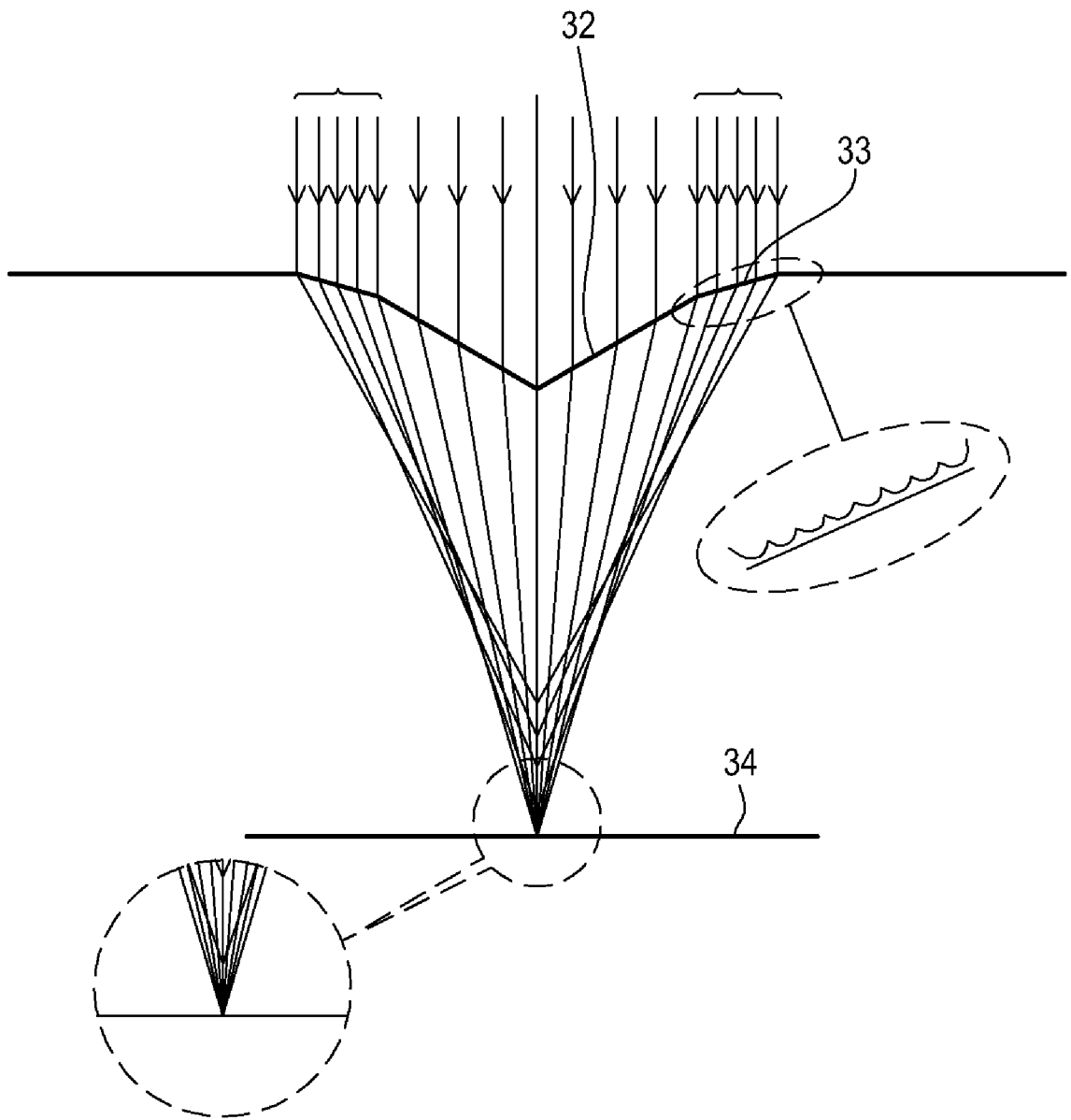
FIG. 10 is an illustration of incidence of light on a correction area and a prevention area formed on an eyeball of a person with myopia in the present invention.

FIG. 10 is an illustration of incidence of light on a correction area and a prevention area formed on an eyeball of a person with myopia. As shown in FIG. 10, the correction area 32 is formed as a concavely curved surface to alleviate the symptom of myopia, and the prevention area 33 on the periphery of the correction area 32 is formed with a plurality of convex arcs to prevent the imaging problem of presbyopia in the future.

Figure 11:
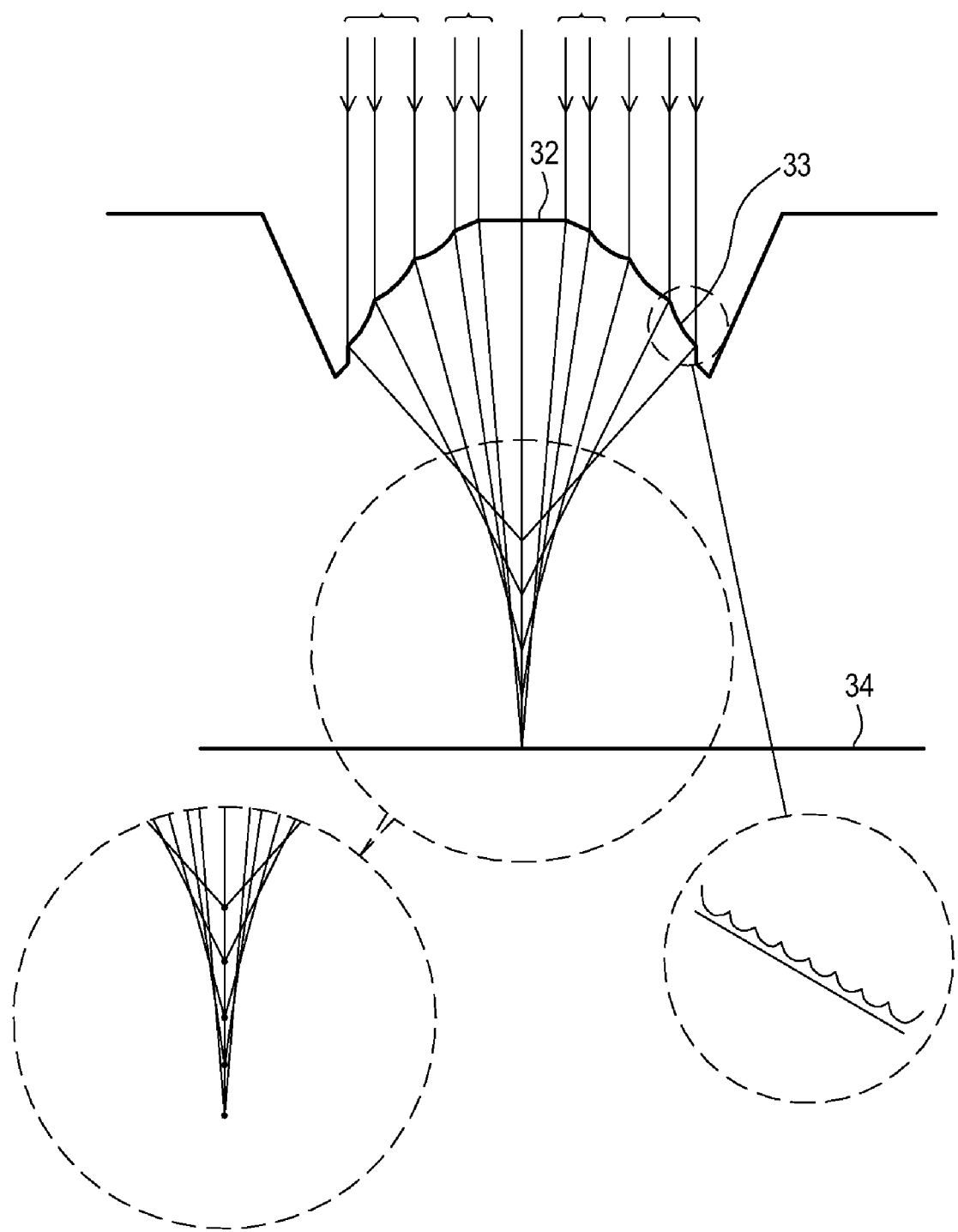
FIG. 11 is an illustration of incidence of light on a correction area and a prevention area are both formed on an eyeball of a person with hyperopia in the present invention.

FIG. 11 is an illustration of incidence on a correction area and a prevention area formed on an eyeball of a person with hyperopia. As shown in FIG. 11, the correction area 32 is formed as a convexly curved surface to alleviate the symptom of hyperopia, and the prevention area 33 on the periphery of the correction area 32 is formed with a plurality of convex arcs to prevent the imaging problem of presbyopia in the future. With the technologies shown in FIGS. 10 and 11, when the positions of the multiple imaging points are pre-defined in front of the retina 34 by the convex arcs, the effect of preventing presbyopia can be achieved in the vision correction for a person with myopia, hyperopia, or astigmatism; moreover, since the prevention area 33 is formed with a plurality of convex arcs to form a plurality of imaging focal points, the problem of presbyopia can be prevented or alleviated for different age groups.

To sum up, a correction area and a prevention area are formed on a cornea of an eye of a person by a laser unit in a vision correction system in the present invention, and if the person has no refractive errors, the prevention area may be formed alone, and imaging focal points are pre-defined through convex arcs on the prevention area, so as to solve the imaging problem of presbyopia as the crystalline lens is deformed due to aging; if the person further has the problem of myopia, hyperopia, or astigmatism, a concavely curved surface, a convexly curved surface, or a level surface may be formed on the correction area at the same time, and multiple convex arcs are formed around the correction area, so as to achieve vision correction and solve the problem of presbyopia in the future at the same time.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A vision correction system, comprising:
    an evaluation device, for scanning an eyeball of a person, and recording a spherical curvature of a cornea of the eyeball as an evaluation data; and
    a correction device, comprising:
        an operation unit, for receiving the evaluation data recorded by the evaluation device and operating on and converting the evaluation data into a correction data; and
        a laser unit, controlled by the operation unit for respectively forming a correction area and a prevention area on the cornea of the eyeball of the person according to the correction data, wherein the prevention area is formed as multiple convex arcs outwards from a periphery of the correction area, and each of the convex arcs has a different radius,
    wherein a first curvature data is pre-calculated by the evaluation device from the periphery of the correction area, and then a first convex arc is formed by cutting the periphery of the correction area according to the first curvature data by the laser unit; a second curvature data is pre-calculated by the evaluation device from a periphery of the first convex arc, and then a second convex arc is formed by cutting the periphery of the first convex arc according to the second curvature data by the laser unit.

2. The vision correction system according to claim 1, wherein a concavely curved surface is formed on the correction area for the person with myopia.

3. The vision correction system according to claim 1, wherein a convexly curved surface is formed on the correction area for the person with hyperopia.

4. The vision correction system according to claim 1, wherein a flat surface is formed on the correction area for the person with astigmatism.

5. The vision correction system according to claim 1, wherein the laser unit comprises a laser beam source for generating an appropriate amount of laser energy.

6. The vision correction system according to claim 5, wherein the laser unit further comprises an optical light guiding module for dispersing laser energy distribution of the laser energy and finally focusing the laser energy on one point.

7. The vision correction system according to claim 1, wherein the correction device is an argon fluoride excimer laser machine, the laser unit in the correction device has an excimer laser, and the excimer laser is split by an optical light guiding module into a plurality of light beams.

8. The vision correction system according to claim 7, wherein the light beams are sequentially or randomly projected, and are projected on both the correction area and the prevention area simultaneously.

9. The vision correction system according to claim 1, wherein the evaluation device is used for evaluating and dividing the correction area and the prevention area on the eyeball.

10. An operating method of a vision correction system, comprising:
    scanning an eyeball of a person and recording a spherical curvature of a cornea of the eyeball as an evaluation data by an evaluation device;
    operating on and converting the evaluation data into a correction data by an operation unit of a correction device; and
    respectively forming a correction area and a prevention area on the cornea of the eyeball of the person according to the correction data by a laser unit of the correction device, wherein the prevention area is formed as multiple convex arcs outwards from a periphery of the correction area, and each of the convex arcs has a different radius,
    wherein a first curvature data is pre-calculated by the evaluation device from the periphery of the correction area, and then a first convex arc is formed by cutting the periphery of the correction area according to the first curvature data by the laser unit; a second curvature data is pre-calculated by the evaluation device from a periphery of the first convex arc, and then a second convex arc is formed by cutting the periphery of the first convex arc according to the second curvature data by the laser unit.

11. The operating method of a vision correction system according to claim 10, wherein a concavely curved surface is formed on the correction area by the laser unit for the person with myopia.

12. The operating method of a vision correction system according to claim 10, wherein a convexly curved surface is formed on the correction area by the laser unit for the person with hyperopia.

13. The operating method of a vision correction system according to claim 10, wherein a flat surface is formed on the correction area by the laser unit for the person with astigmatism.

14. The operating method of a vision correction system according to claim 10, wherein a third curvature data is pre-calculated by the evaluation device from a periphery of the second convex arc, and then a third convex arc is formed by cutting the periphery of the second convex arc according to the third curvature data by the laser unit.

* * * * *